(12) United States Patent
Jacobson (10) Patent No.: US 7,276,338 B2
(45) Date of Patent: Oct. 2, 2007

(54) NUCLEOTIDE SEQUENCING VIA REPETITIVE SINGLE MOLECULE HYBRIDIZATION

(76) Inventor: Joseph M. Jacobson, 223 Grant Ave., Newton, MA (US) 02459

( * ) Notice: Subject to any disclaimer, the term of this patent is extended or adjusted under 35 U.S.C. 154(b) by 192 days.

(21) Appl. No.: 10/990,939

(22) Filed: Nov. 17, 2004

(65) Prior Publication Data
US 2005/0153324 A1    Jul. 14, 2005

Related U.S. Application Data

(60) Provisional application No. 60/520,751, filed on Nov. 17, 2003.

(51) Int. Cl.
  *C12Q 1/68*  (2006.01)
  *C12P 19/34*  (2006.01)
(52) U.S. Cl. .......................... 435/6; 435/91.1
(58) Field of Classification Search ............... None
See application file for complete search history.

(56) References Cited

U.S. PATENT DOCUMENTS

| | | | |
|---|---|---|---|
| 5,202,231 A | 4/1993 | Drmanac et al. | 435/6 |
| 5,492,806 A | 2/1996 | Drmanac et al. | 435/6 |
| 5,525,464 A | 6/1996 | Drmanac et al. | 435/6 |
| 5,667,972 A | 9/1997 | Drmanac et al. | 435/6 |
| 5,695,940 A | 12/1997 | Drmanac et al. | 435/6 |
| 5,972,619 A | 10/1999 | Drmanac et al. | 435/6 |
| 6,018,041 A | 1/2000 | Drmanac et al. | 435/6 |
| 6,025,136 A | 2/2000 | Drmanac | 435/6 |
| 6,268,210 B1 | 7/2001 | Baier et al. | 435/288.5 |
| 6,270,961 B1 | 8/2001 | Drmanac | 435/6 |
| 6,297,006 B1 | 10/2001 | Drmanac et al. | 435/6 |
| 6,300,076 B1 * | 10/2001 | Koster | 435/6 |
| 6,309,824 B1 | 10/2001 | Drmanac | 435/6 |
| 6,316,191 B1 | 11/2001 | Drmanac et al. | 435/6 |
| 6,383,742 B1 | 5/2002 | Drmanac et al. | 435/6 |
| 6,401,267 B1 | 6/2002 | Drmanac | 435/6 |
| 6,403,315 B1 | 6/2002 | Drmanac | 435/6 |
| 6,451,996 B1 | 9/2002 | Drmanac et al. | 536/24.3 |
| 6,480,791 B1 * | 11/2002 | Strathmann | 702/20 |
| 6,537,755 B1 | 3/2003 | Drmanac | 435/6 |

FOREIGN PATENT DOCUMENTS

WO   WO 2004/076683 A2   9/2004

* cited by examiner

*Primary Examiner*—James Martinell (57) ABSTRACT

Methods of obtaining sequence information about target oligonucleotides by repetitive single molecule hybridization are disclosed. The methods include exposing a target oligonucleotide to one or more copies of a test oligonucleotide; measuring hybridization; dehybridizing the test oligonucleotide; and repeating until the information content from the hybridization trials equals or exceeds the information content of the target oligonucleotide.

21 Claims, 14 Drawing Sheets

| M | Number of M-mers in Library |
|---|---|
| 1 | 4 |
| 2 | 16 |
| 3 | 64 |
| 4 | 256 |
| 5 | 1024 |
| 6 | 4096 |
| 7 | 16384 |
| 8 | 65536 |
| 9 | 262144 |
| 10 | 1048576 |
| 11 | 4194304 |
| 12 | 16777216 |
| 40 | 1.20893E+24 |

| N | $Log_2(4^N)$ | M* | I(M*,N) | $4^{M*} \times$ I(M*,N) | M*+1 | I(M*+1,N) | $4^{(M*+1)} \times$ I(M*+1,N) |
|---|---|---|---|---|---|---|---|
| 10 | 20 | 2 | 0.99 | 16 | 3 | 0.52 | 34 |
| 18 | 36 | 2 | 0.92 | 15 | 3 | 0.77 | 49 |
| 50 | 100 | 3 | 1.00 | 64 | 4 | 0.65 | 167 |
| 100 | 200 | 4 | 0.90 | 230 | 5 | 0.43 | 445 |
| 1000 | 2000 | 5 | 0.96 | 980 | 6 | 0.75 | 3081 |
| 10000 | 20000 | 7 | 0.99 | 16295 | 8 | 0.59 | 38533 |

Figure 6B

| M | $N_{Max}$ | $4^M \times I(M, N_{MAx})$ | $N_{Optimal}$ | $4^M \times I(M, N_{Optimal})$ |
|---|---|---|---|---|
| 2 | 7 | 14 | 4 | 11 |
| 3 | 30 | 60 | 13 | 40 |
| 4 | 121 | 243 | 48 | 163 |
| 5 | 489 | 979 | 184 | 653 |
| 6 | 1961 | 3923 | 723 | 2606 |

NUCLEOTIDE SEQUENCING VIA REPETITIVE SINGLE MOLECULE HYBRIDIZATION

REFERENCE TO RELATED APPLICATIONS

This application claims the benefit of and priority to U.S. application Ser. No. 60/520,751, filed Nov. 17, 2003, which is hereby incorporated by reference in its entirety into the present application for all purposes.

BACKGROUND

The advent of the first reference sequence of the human genome by Lander (*Nature* (15 Feb. 2001) 409: 860-921) and Venter (*Science* (16 Feb. 2001) 291:1304) has generated increased interest in the ability to sequence entire genomes which range in size from ~1 megabase to as high as 600 gigabases in some organisms. To make uses of the human genome reference sequence tractable, several important innovations including highly parallel capillary electrophoresis were developed in order to bring base sequencing costs down.

Unfortunately, to go beyond a small number of reference sequences to the point where it is feasible to sequence each individual genome in a population or to sequence ab initio a large class of new organisms, vastly faster and less expensive means are required. Towards that end several new approaches have been proposed and demonstrated to various degrees including: Edman degradation and fluorescent dye labeling of a single DNA strand in a flow cytometer; "sequencing by hybridization" (Perlegen Corp.; Callida Genomics) and "sequencing by synthesis" (Quake et al., Cal. Tech.; Solexa Corp.). The latter two approaches afford a high degree of parallel information retrieval, leveraging chip-based imaging system approaches to simultaneously record data from a very large number of gene chip pixels. Unfortunately, each approach suffers several shortcomings.

"Sequencing by hybridization" requires an inordinately large array of explicitly patterned spots to approximate the information content of the genome to be sequenced. In addition, oligonucleotides from the sample are required to search a very large array of gene chip oligonucleotide complements, making hybridization time very long.

"Sequencing by synthesis" avoids a number of the issues above but introduces difficult and error-prone chemistries which may be difficult to scale effectively.

SUMMARY OF THE INVENTION

The present invention provides "repetitive single molecule hybridization," wich has the ability to carry out de novo sequencing of DNA, such as genomic DNA, at high speed and low cost.

The invention involves obtaining sequence information from a target nucleotide. A plurality of target nucleotides can be interrogated in parallel using the methods described herein, permitting the sequencing of an entire genome or a subset thereof. Generally, test oligonucleotides from a library of test oligonucleotides of uniform length are exposed to one or more target oligonucleotides under conditions permitting hybridization of the test oligonucleotides to a perfectly complementary sequence. The target nucleotide can be immobilized on a chip such as an inverse gene chip representing a genome or a portion thereof. A suitable inverse gene chip can be prepared, for example, by dehybridizing (denaturing) nucleic acids (e.g. by increasing the temperature or altering solvent conditions), selecting a single strand, cutting the strand into target oligonucleotides of average length N nucleotides and chemically attaching the target nucleotides to a substrate.

To perform sequencing, a target oligonucleotide is exposed under hybridizing conditions to a first set of identical test oligonucleotides drawn from a library of all possible test oligonucleotides of length M. Hybridization or failure to hybridize at the single molecule level is detected and recorded. The molecules are denatured to separate any annealed oligonucleotides and the first set of test oligonucleotides is then washed away. The process is repeated, substituting different sets of identical test oligonucleotides, until the library of test oligonucleotides has been exhausted or until the information content of the set of hybridization experiments equals or exceeds the targeted sequence information.

The present invention permits highly parallel sequencing of target nucleic acids while requiring a library of test oligonucleotides of only modest size. Accordingly, in one embodiment, where the target oligonucleotides are less than 50 nucleotides in length (i.e. N<50), test oligonucleotides having 2, 3, or 4 potentially informative positions (i.e. the oligonucleotide length, subtracting uninformative spacer positions, universal bases, positions hybridizing to any primer sequences incorporated in the target oligonucleotides, or the like) are used; where the target oligonucleotides are 50-99 nucleotides in length, test oligonucleotides having 3, 4, or 5 potentially informative positions are used; where the target oligonucleotides are 100-999 nucleotides in length, test oligonucleotides having 4-6 potentially informative positions are used; where the target oligonucleotides are 1,000-10,000 nucleotides in length, test oligonucleotides having 5-8 potentially informative positions are used; and where the target oligonucleotides are greater than 10,000 nucleotides in length, test oligonucleotides having 7-13 potentially informative positions are used. In another embodiment, positive hybridization outcomes are used to deduce a set of possible target oligonucleotide sequences and negative hybridization outcomes are used to eliminate members from the set.

To address the existence of repeats in some nucleic acids of interest, the invention also provides methods of sequencing using test oligonucleotides incorporating one or more spacers separating at least two of the potentially informative positions of the test oligonucleotides. Useful spacers include, for example, double-stranded portions of the test oligonucleotide; spacers comprising an abasic furan; or other traditional chemical spacers such as those incorporating a polyethylene glycol portion or an extended carbon chain including, for example, at least three methylene groups.

BRIEF DESCRIPTION OF THE DRAWINGS

FIGS. 2A-2E schematically illustrate the steps involved in deriving de novo sequence information from an inverse gene chip by means of repeated test hybridizations with members of the library of all possible oligonucleotides of length M ("M-mers").

DETAILED DESCRIPTION OF THE INVENTION

Figure 1A:
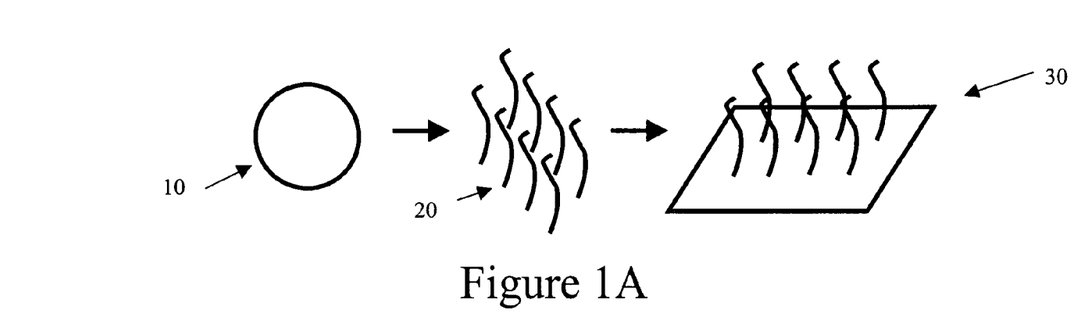
FIG. 1A is a schematic representation of preparation of an inverse gene chip.
Figure 1B:
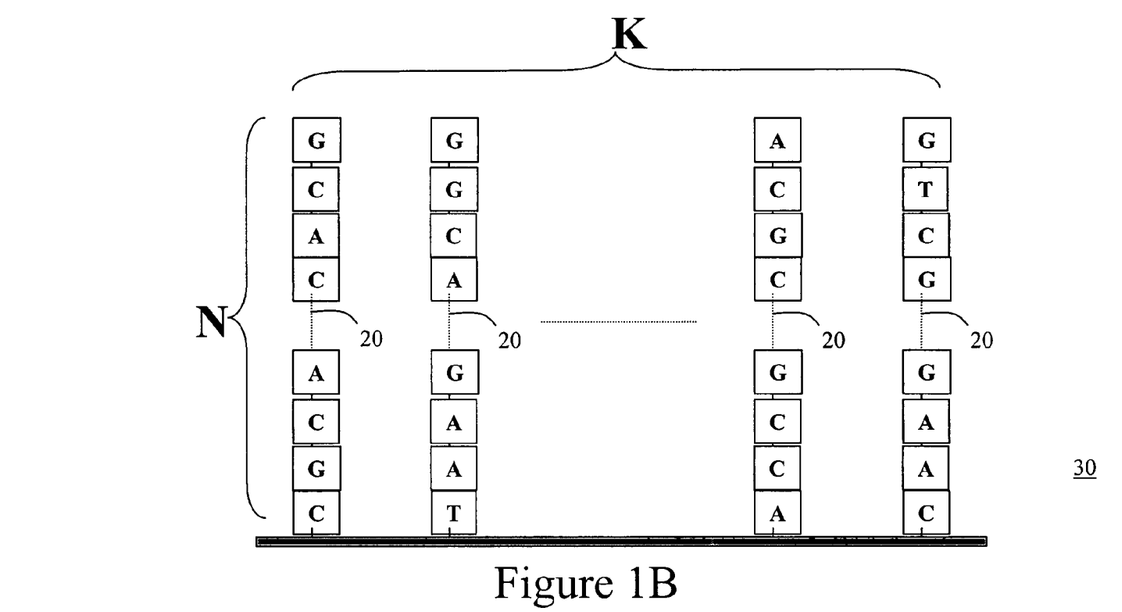
FIG. 1B is a close-up schematic of an inverse gene chip consisting of K oligonucleotides of average length N derived from target genome disposed at random fixed locations.

An inverse gene chip is known in the field and has been employed in the technique termed "sequencing by synthesis" (see Quake et al., *PNAS* 100:3960; Solexa Corp.). FIG. 1A illustrates an exemplary technique for producing a gene chip. A cell 10 is lysed and its genomic DNA separated. In many cases (other than for single-stranded DNA viruses) the DNA will be in double-stranded form. The DNA may be dehybridized either using heat (melting) or chemically or enzymatically to isolate a single strand of the genomic DNA. The genomic DNA is then cut into oligonucleotides of average size N. In addition to other techniques known in the literature, one can create a chimera consisting of an oligonucleotide coupled to a nuclease. The chimera will bind periodically to the DNA and cut locally, thus processing the single stranded genomic DNA into a series of oligonucleotide fragments 20. We refer to the genomic oligonucleotide fragments 20 as target fragments. These target fragments are then immobilized on a support by standard 3' or 5' coupling chemistry to form an inverse gene chip 30. FIG. 1B is a schematic close-up view of an inverse gene chip 30 consisting of K target oligonucleotides 20 of average length N nucleotides. K is varied based on the amount of nucleic acid sequence information desired and the average length N of the nucleotides; for maximum throughput, however, K is selected to approach the resolving capacity of the imaging system used.

Figure 2A:
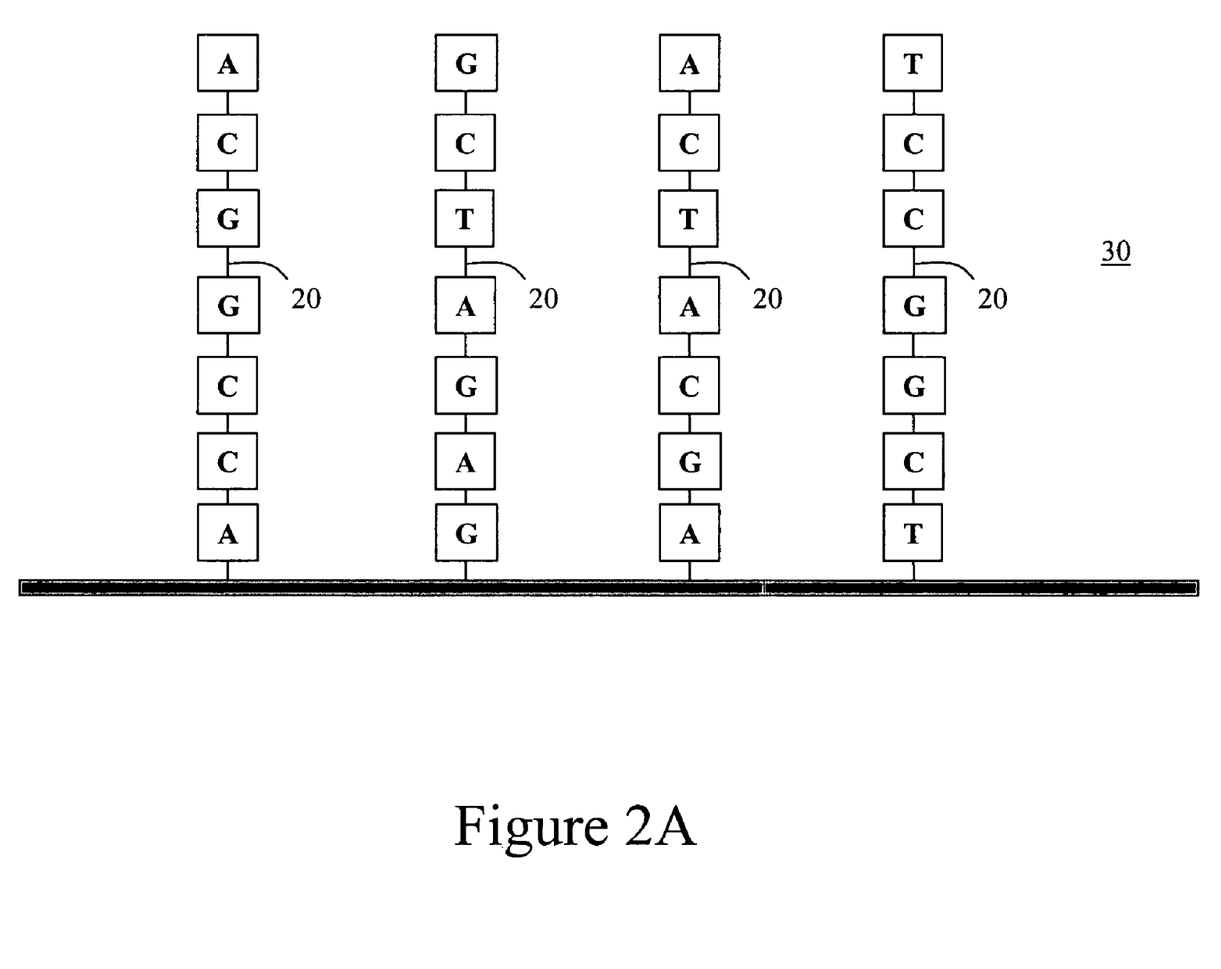
FIG. 2A depicts the initial condition before incubation with test M-mers.
Figure 2B:
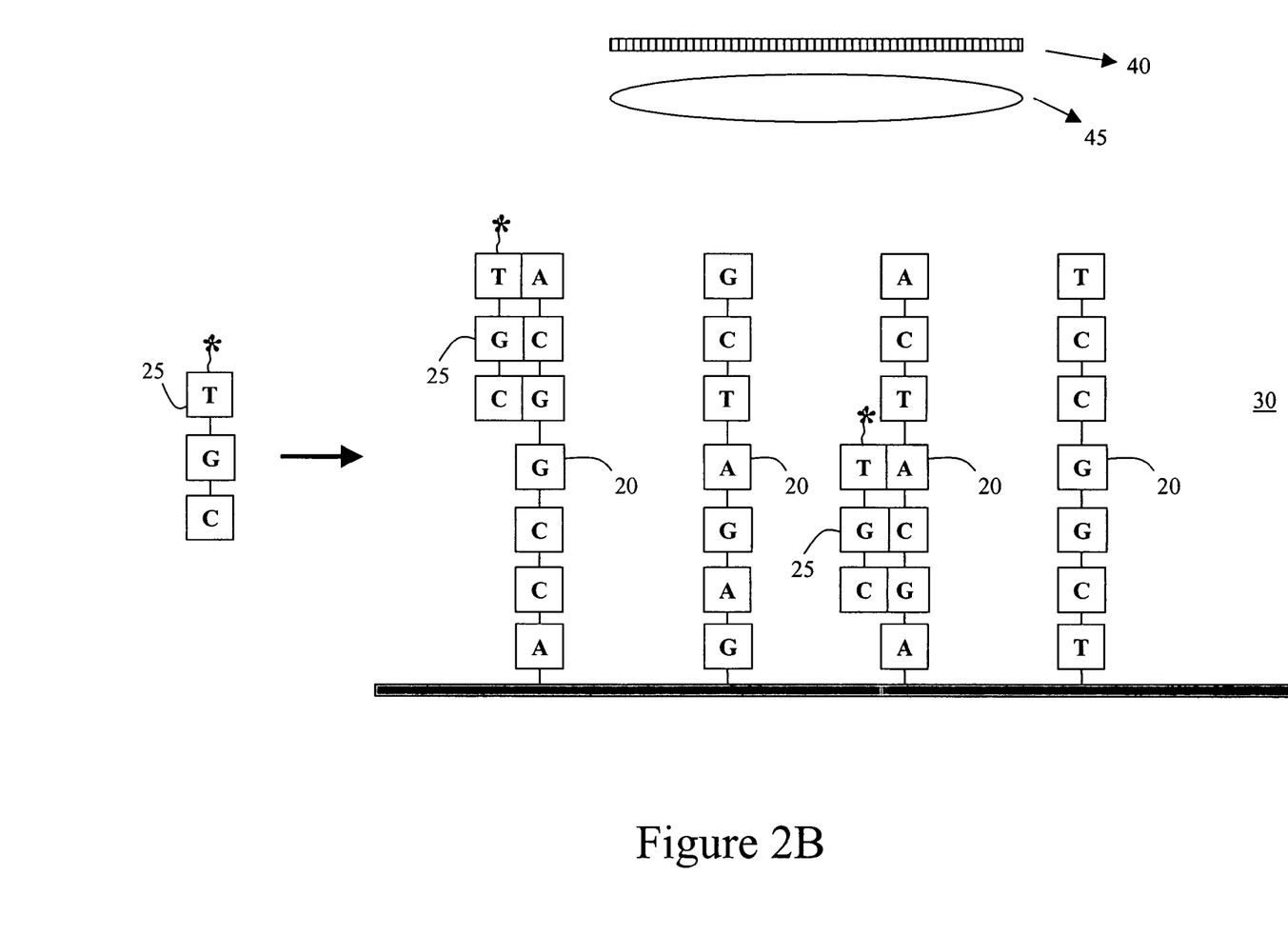
FIG. 2B depicts introduction of a test M-Mer oligonucleotide with fluorescent dye under selective hybridizing conditions and depicts the subsequent parallel readout with an electronic imager.
Figure 2C:
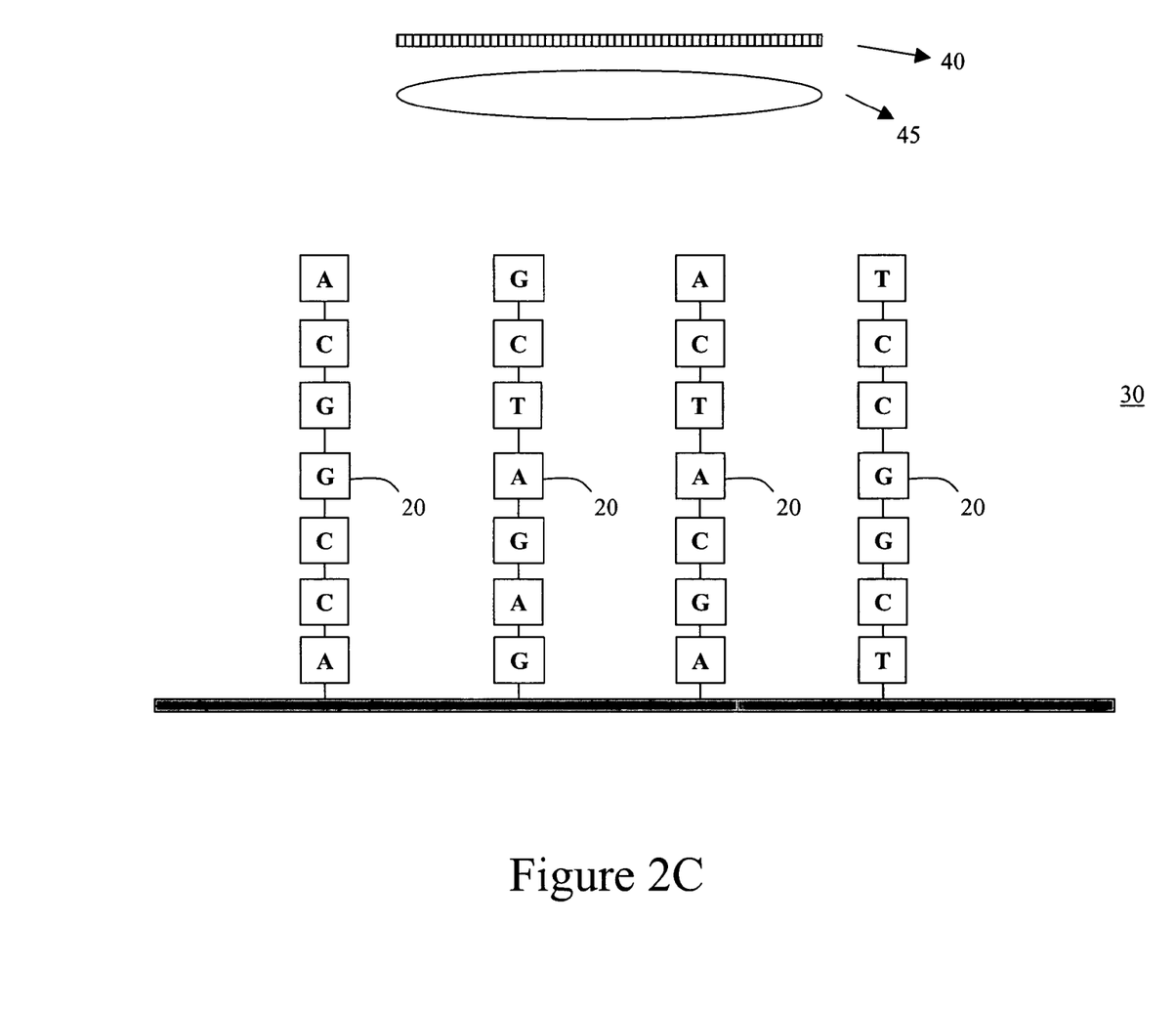
FIG. 2C depicts the status following dehybridization and wash steps.
Figure 2D:
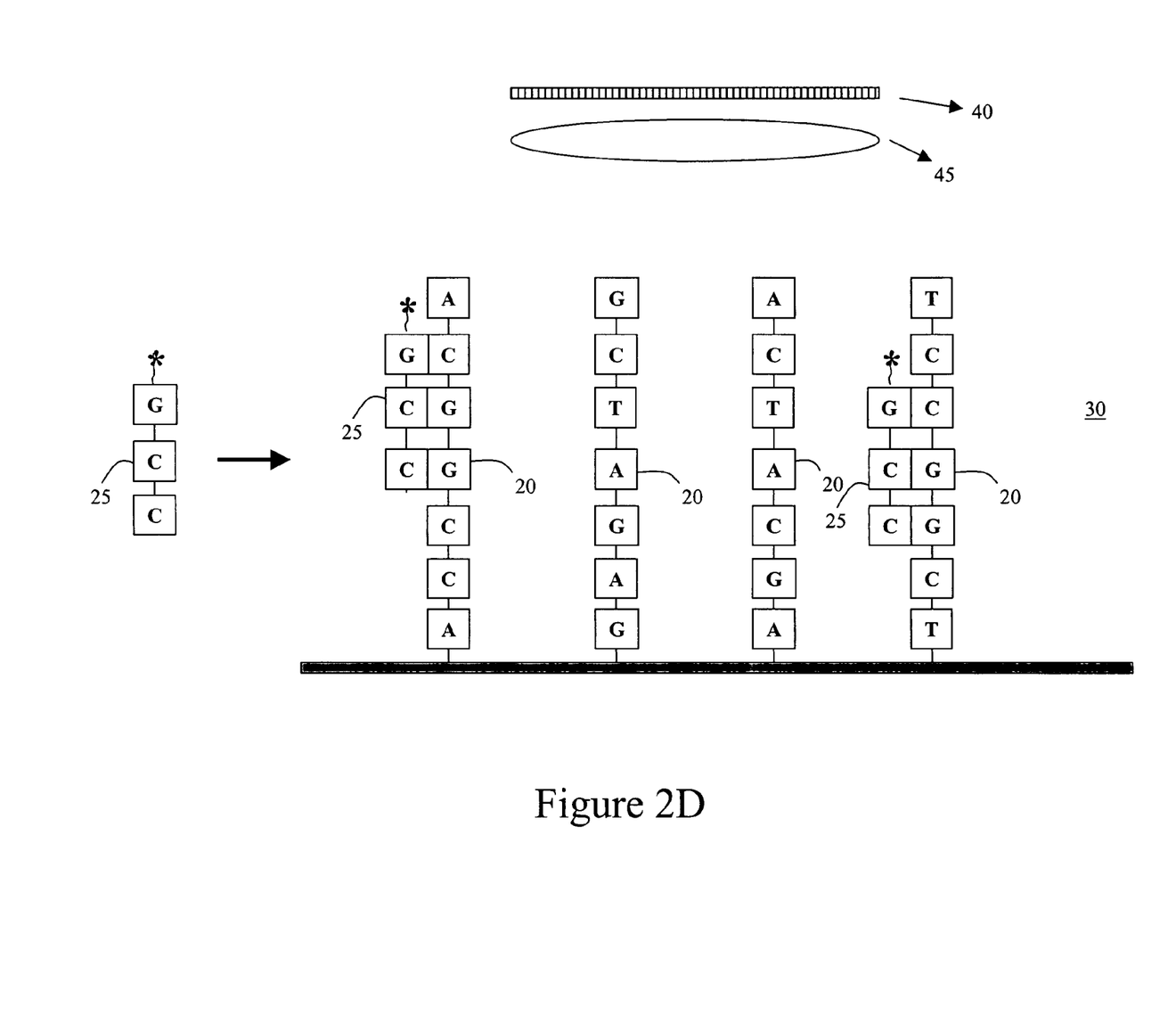
FIG. 2D depicts the introduction a second test M-Mer oligonucleotide under selective hybridizing conditions and depicts the subsequent parallel readout with the electronic imager.

FIGS. 2A-2E schematically illustrate the steps involved in obtaining the data required to extract de novo sequence information from DNA. FIG. 2A depicts the initial condition before incubation with test M-Mers. FIG. 2B depicts introduction of a test M-Mer oligonucleotide 25 with fluorescent dye under selective hybridizing conditions and subsequent parallel readout with a conventional electronic imager 40. Electronic imager 40 can incorporate a lens 45 to image inverse gene chip 30 or can operate without a lens, in which case electronic imager 40 is located in close proximity to inverse gene chip 30. FIG. 2C shows the conditions after a subsequent dehybridization and wash step; the oligonucleotide fragments return to the unbound state as previously shown in FIG. 2A. FIG. 2D depicts the introduction of a second test M-Mer oligonucleotide 25 under selective hybridizing conditions and subsequent parallel readout with electronic imager 40. Readout involves detecting the presence or absence of a fluorescent signal for each position of inverse gene chip 30 associated with a target oligonucleotide 20 and recording the presence or absence of a fluorescent signal, generally in a computer-readable medium. Steps c and d are repeated with subsequent M-mer oligonucleotides until sufficient information is extracted.

Figure 2E:
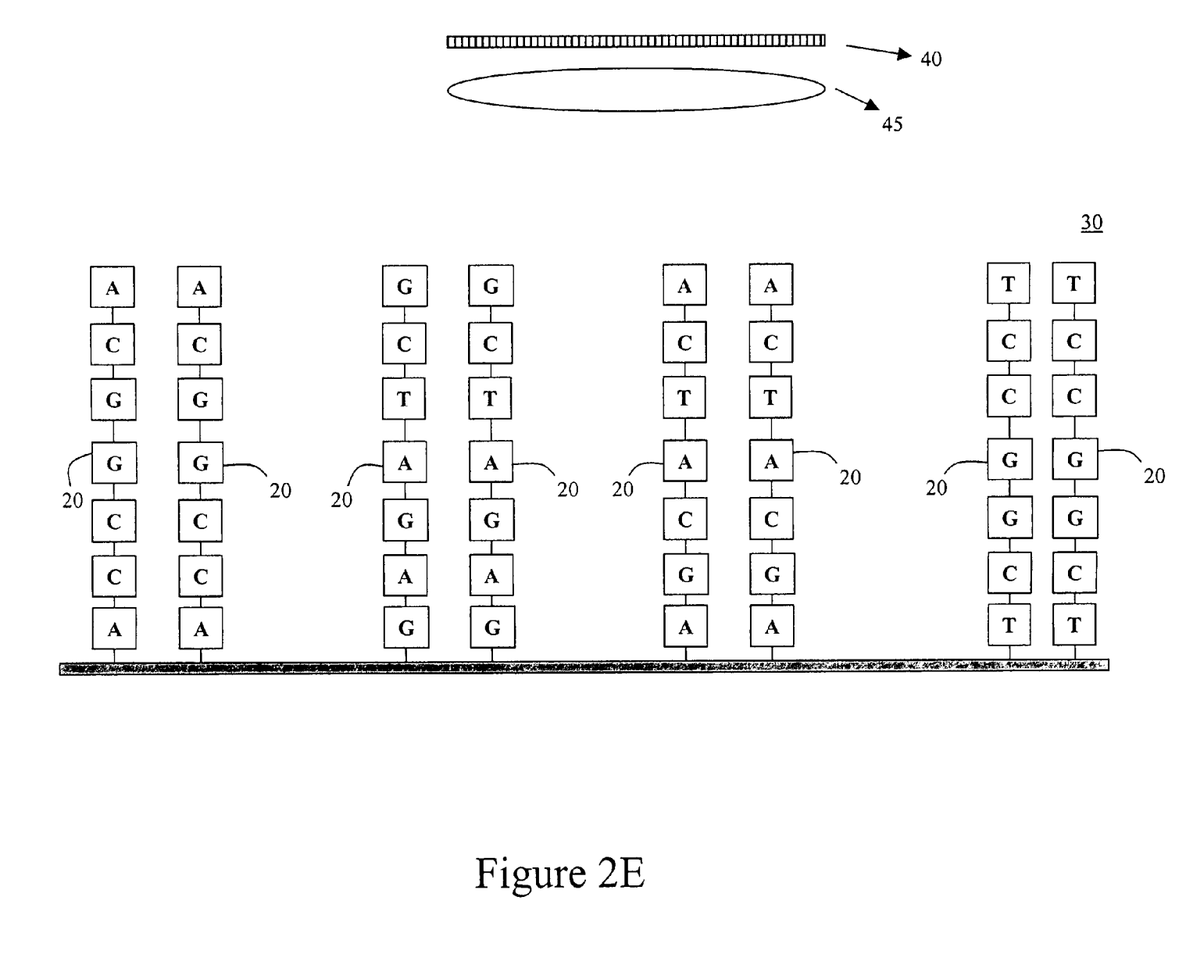
FIG. 2E is a schematic depiction of an inverse DNA chip with multiple copies of target N-mer oligonucleotides.

Referring to FIG. 2E, it may be convenient in certain cases not to require single molecule hybridization detection. In this case a plurality of co-located (i.e. located in physical proximity to each other) copies of target oligonucleotides 20 can be used. Such multiple co-located target oligonucleotides 20 can be readily generated by, for example, local PCR such as that enabled by rolling circle polymerization.

Figure 3:
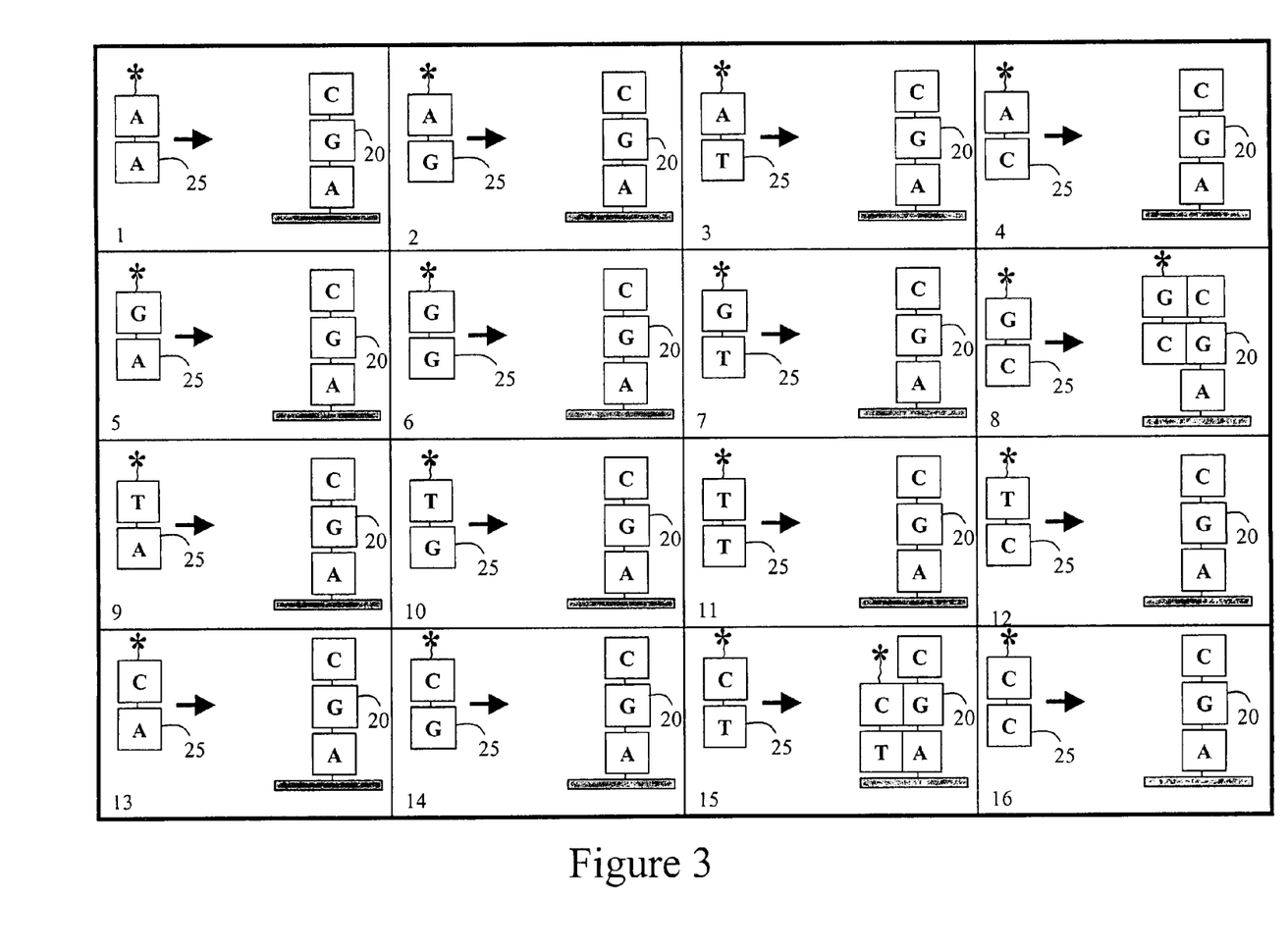
FIG. 3 is a schematic example showing the extraction of 16 bits of hybridization information sufficient for uniquely determining the 6 bits of sequence information of the target 3-mer.

FIG. 3 is a schematic example showing the extraction of 16 bits of hybridization information sufficient for uniquely determining the 6 bits of sequence information of the target 3-mer 20. There are $4^2$ (sixteen) possible 2-mer test oligonucleotides 25, each of which is sequentially incubated with the target 3-mer 20, in this case the nucleotide sequence C-G-A. Only in cases 8 and 15 is hybridization successful; the positive and negative hybridization outcomes of all sixteen exposure events are detected and recorded. If, for example, one were to write a bit sequence consisting of 0's in the case of no hybridization and 1's in the case of successful hybridization for each of the sixteen possible test oligonucleotides 25, then one would have the bit sequence 0000000100000010. This bit sequence, representing all possible hybridization trials from the 2-mer library contains approximately 16 bits of information (I explain below why this is only an approximate information measure), which is larger than the information content of the target 3-mer sequence, CGA, which contains $\log_2(4^3)=6$ bits of information. Thus, in most cases a 2-mer library can uniquely decode a 3-mer target sequence. In contrast, a palindromic sequence such as CGC cannot be uniquely decoded using only a 2-mer library because both it and the sequence GCG bind the same set of 2-mers (namely CG and GC). Such cases can be disambiguated by applying M-mer libraries of different size coupled with the ability to determine the number of test oligonucleotides bound to a given target oligonucleotide 20. For instance, in this case, applying a 1-mer library disambiguates CGC from GCG, as 2 G's would bind to the former and only one would bind to the latter.

The procedure for determining sequence information about target oligonucleotide 20 from the test bit sequence requires ordering in an overlapping manner the test oligonucleotides that successfully hybridized. Thus we know from the test data that the sequence of target oligonucleotide 20 has both a CG and a GA with the only overlap at G, giving the unique sequence of CGA. The section discussing FIGS. 7 and 8 details the procedure and flowchart algorithm for determining sequences from test hybridization data.

Figure 4:
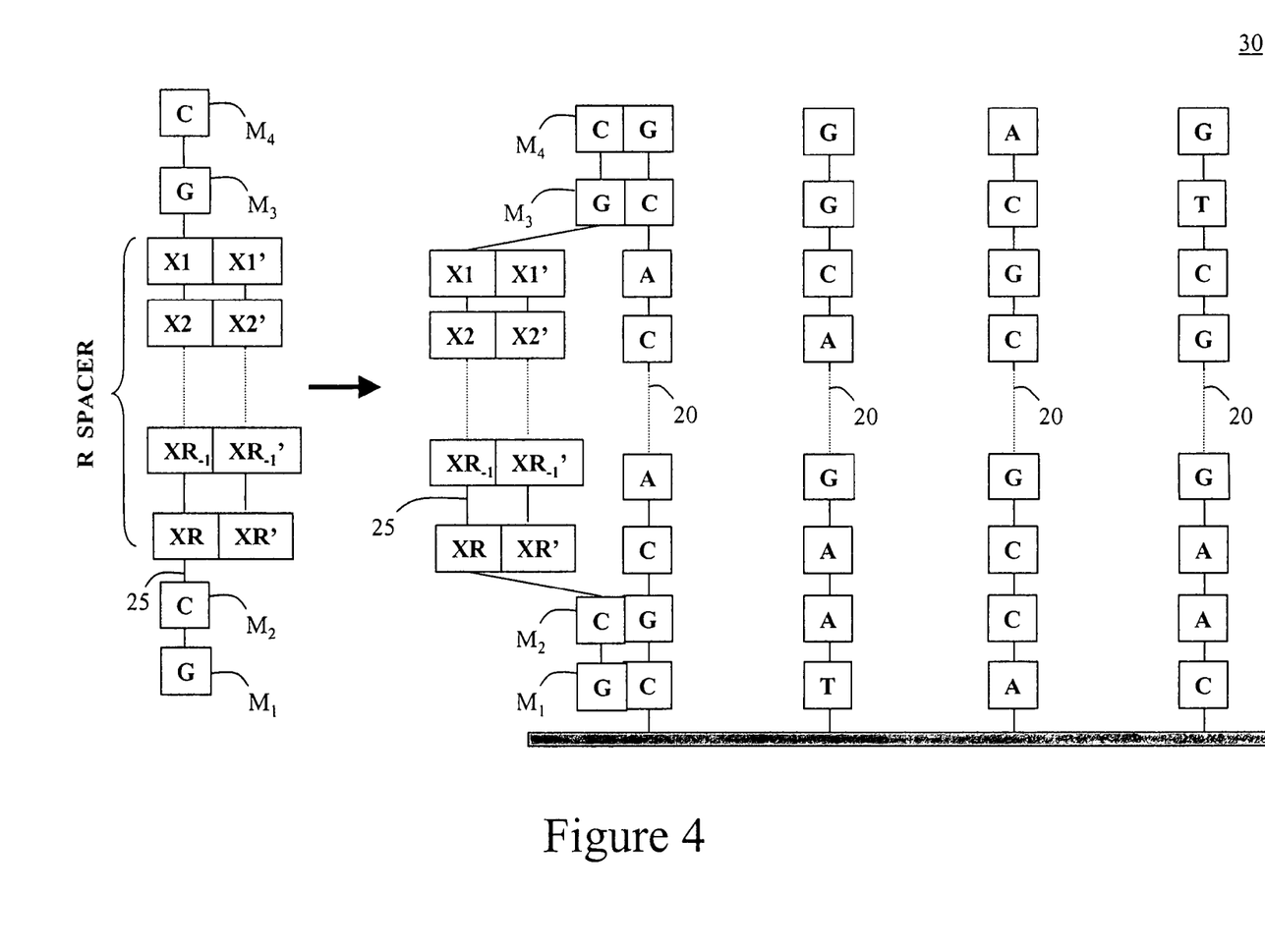
FIG. 4 is a schematic of an M-mer oligonucleotide interposed with an R-mer double stranded spacer.

Referring to FIG. 4, there are areas of certain genomes with long repeat sequences, longer than the sizes of target oligonucleotides 20 that can be conveniently handled by a typical M-mer library. In such cases the M interrogating nucleotides of test oligonucleotide 25 may be interspaced with a spacer of length R as depicted in FIG. 4. This allows M-mer 20 to bridge larger target oligonucleotides 20. By combining data obtained with M-mer libraries containing different spacer values R full sequence data can be obtained. The spacer may consist of double stranded nucleotide sequences as shown in FIG. 4 which do not interact with target oligonucleotide 20, or it may contain a minimally interacting single stranded sequence, such as a sequence comprising one or more abasic furans, or a sequence to which is bound another hybridization blocker such as a sequence-specific protein binder or a sequence-specific zinc finger complex. Exemplary spacers can, for example, be constructed by incorporating one of the following moieties during synthesis of a test oligonucleotide 25: 3,6,9-trioxaundecane-1,11-diisocyanate; 5'-O-dimethoxytrityl-1',2'-dideoxyribose-3'-[(2-cyanoethyl)-(N,N-diisopropyl)]-phosphoramidite; 3-(4,4'-dimethoxytrityloxy)propyl-1-[(2-cyanoethyl)-(N,N-diisopropyl)]-phosphoramidite; 9-O-dimethoxytrityl-triethyleneglycol, 1-[(2-cyanoethyl)-(N,N-diisopropyl)]-phosphoramidite; 12-(4,4'-dimethyoxytrityloxy)dodecyl-1-[(2-cyanoethyl)-(N,N-diisopropyl)]-phosphoramidite; or 18-O-dimethoxytritylhexaethyleneglycol, 1-[(2-cyanoethyl)-(N, N-diisopropyl)]-phosphoramidite. Alternatively, the target oligonucleotides themselves can have an R-mer cut out of them, where R corresponds to a length of the target oligonucleotide known to have repetitive or uninformative nucleotide positions.

Figure 5:
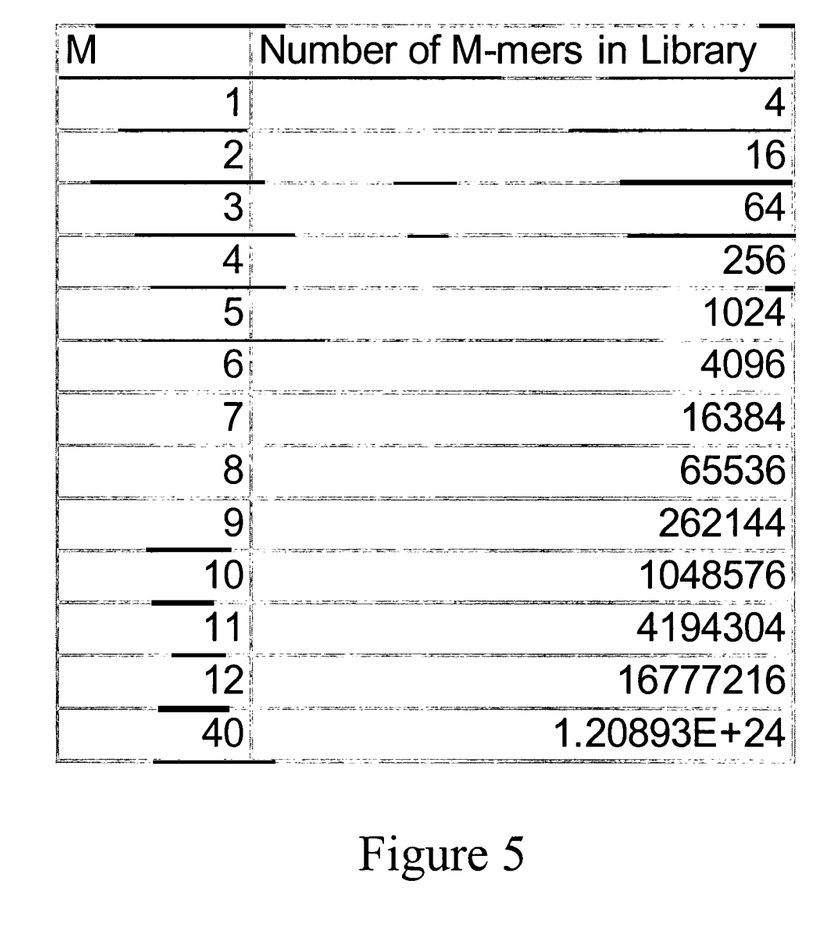
FIG. 5 is a table of M-mer library size as a function of M.

FIG. 5 is a table of the size of the M-mer library of test oligonucleotides as a function of M assuming the nucleotide at any position is chosen from a possible set of 4. The size of the library is simply the number of all possible oligonucleotides of length M which for the case of h different types of nucleotides is given by $h^M$. For most natural systems h=4 (i.e. adenine, guanine, cytosine, and either thymine or uracil). For many applications it will be useful to deliver test oligonucleotides to the inverse gene chip array by means of microfluidics. Practical considerations of delivering test oligonucleotides, time to deliver them as well as time and cost to generate the library coupled with the number of elements in a single molecule hybridization detection system make library sizes of $M \leq 8$ a good choice.

Figure 6A:
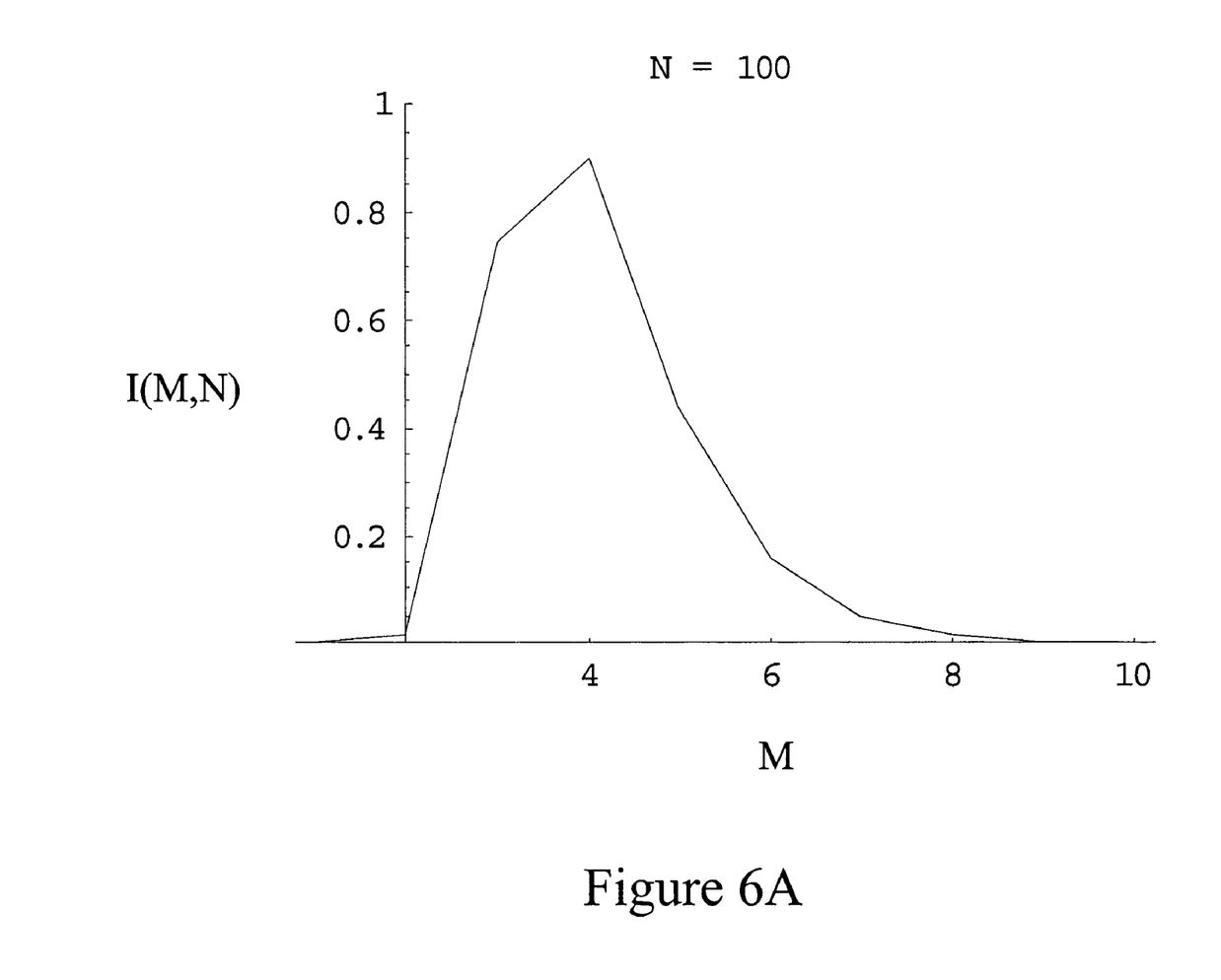
FIG. 6A is a graphical representation of information content in bits per hybridization trial as a function of M where N is fixed at 100.
Figure 6B:
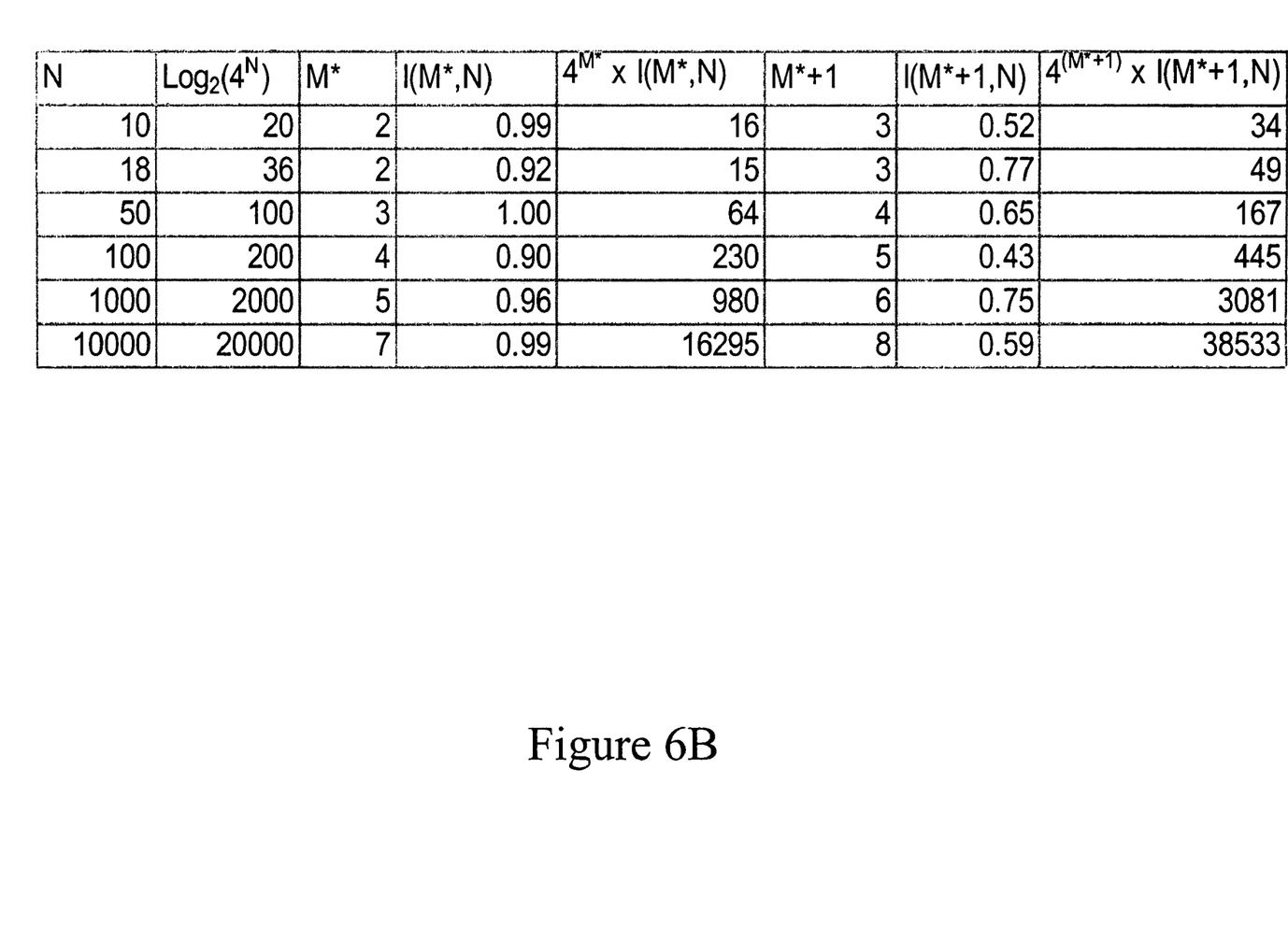
FIG. 6B is a table of optimal values of M for various values of target oligonucleotide length N.
Figure 6C:
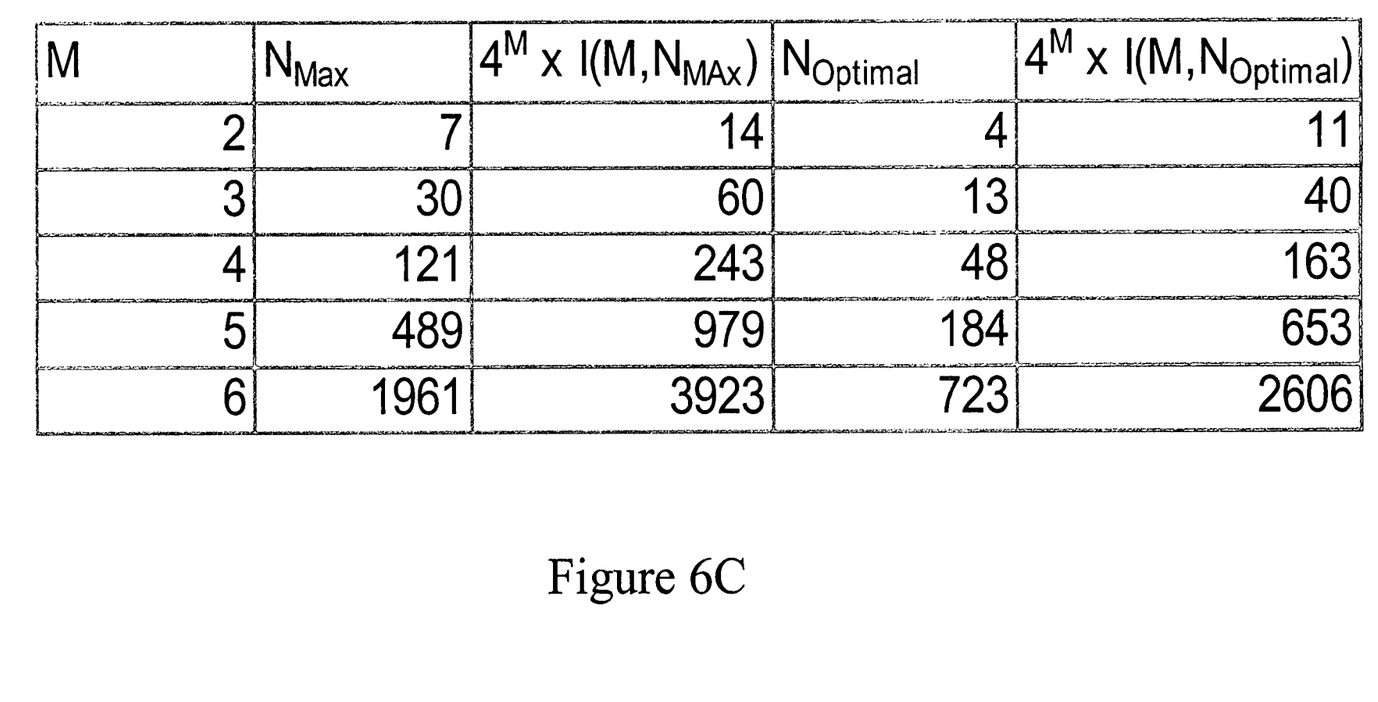
FIG. 6C is a table of maximum and optimal target oligonucleotide sizes N for various values of test oligonucleotide length M.

FIGS. 6A-6C relate to the information content of hybridization experiments of an M-mer test library on an N-mer target oligonucleotide. Knowledge of the information content is a guide to appropriate and preferred values for M in order to obtain full de novo sequence information from an N-mer.

The probability of fully hybridizing a random M-mer somewhere on a given N-mer is given by $$P(M,N)=1-[1-(1/h)^M]^{(N-M+1)} \qquad \text{Eq. 1}$$

where for the case of 4 nucleotides we have h=4.

The information content in bits extractable per test hybridization is given by $$I(M, N) = \text{Log}_2\left(\frac{1}{P(M, N)}\right) P(M, N) + \text{Log}_2\left(\frac{1}{1 - P(M, N)}\right)(1 - P(M, N)) \qquad \text{Eq. 2}$$

as derived from analysis used to analyze the statistics of the information content from a series of weighted coin flips as is known in the art. Thus the total number of bits extractable from the $h^M$ possible hybridization trials is given by $$I(M,N)h^M \qquad \text{Eq. 3}$$

The information content in bits of an N-mer oligonucleotide is given by $$\text{Log}_2(h^N) \qquad \text{Eq. 4}$$

In order to obtain full de novo sequence information of a given target N-mer oligonucleotide we thus require that:

$$I(M,N) \times t \geq \text{Log}_2(h^N) \qquad \text{Eq. 5}$$

where t is the number of hybridization trials noting that a maximum of $t=h^M$ independent trials are possible.

FIG. 6A is a plot of the information content in bits per hybridization trial as a function of M. As shown there is an optimal M (labeled M*) which yields the highest information content per trial. Too small an M or too large an M yields non-optimal information content per trial.

FIG. 6B gives M* for various values of the target oligonucleotide length N. Since one is limited to $h^M$ hybridization trials, an ideal strategy is to employ all possible M* trial hybridizations and then to employ a sufficient number of M*+1 trials (i.e. trials using test oligomers of length M*+1) such that the information content of the hybridization trials equals or exceeds the information content of the target oligonucleotide which one desires to sequence. Accordingly, when the average or maximum length of the target oligonucleotides 20 to be sequenced is less than 50, M is advantageously 2-4; when N is 50-99, M is advantageously 3-5; when N is 100-999, M is advantageously 4-6; when N is 1,000-10,000, M is advantageously 5-8; and when N is greater than 10,000, M is advantageously 7-13.

FIG. 6C is a table calculating $N_{max}$, defined as the largest N such that $I(M,N)4^M > 2N$ for various values M of the size of the test oligonucleotides. $N_{max}$ represents the largest possible N that can be sequenced by means of the data set derived from sequentially testing the hybridization of all possible M-mers on the target N-mer. Although target oligonucleotides are most often no more than 10,000 nucleotides in length (e.g. tens, hundreds, or thousands of nucleotides as shown in FIG. 6C), their length is in fact limited only by the constraints of Eq. 5.

An additional parameter, $N_{Optimal}$, which is defined as $\text{MAXIMUM}[I(M,N)4^M - 2N]$, is also calculated. $N_{Optimal}$ is the value of N which maximizes the difference in information content between the hybridization trials and the target oligonucleotide of size N.

Figure 7:
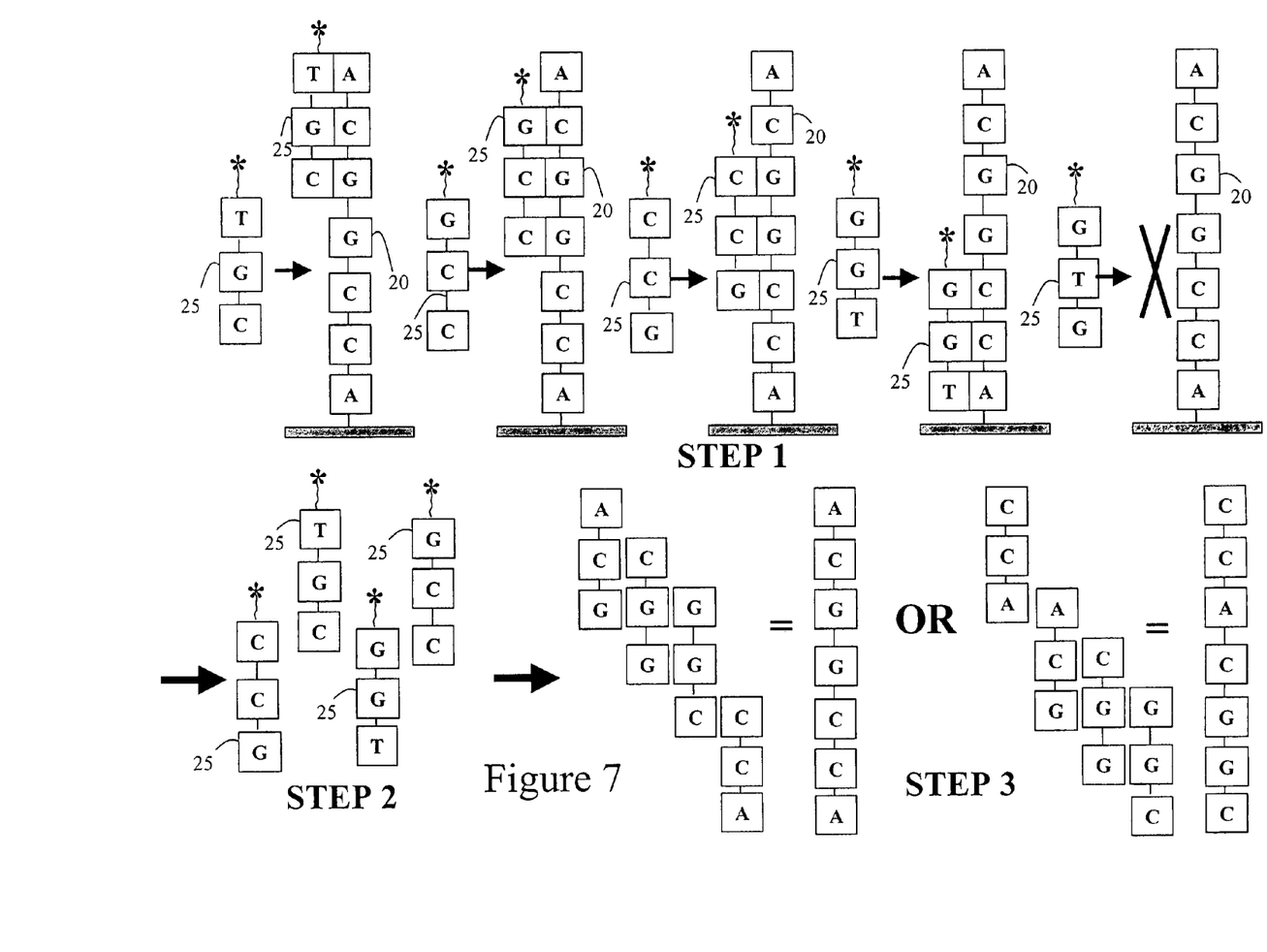
FIG. 7 schematically depicts an example of a procedure for recovering sequence information.
Figure 8:
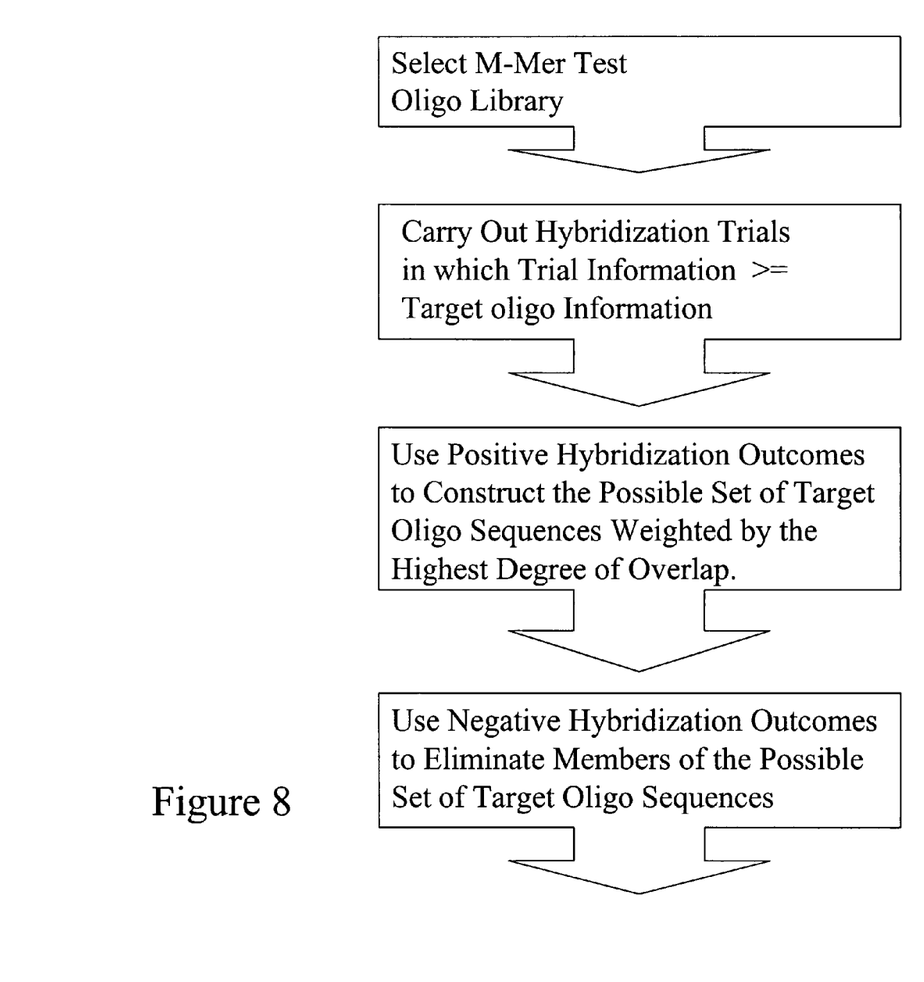
FIG. 8 is a flowchart depicting an algorithm for recovering sequence information.

Referring to FIGS. 7 and 8 an example procedure and flowchart algorithm for inverting the series of hybridization trials and deriving de novo sequence information are given.

Referring to FIG. 7, the example given is the de novo sequence determination of a target 7-mer 20 using 3-mer test oligonucleotides 25. According to Eq. 4 the information content of an 7-mer is 14 bits. According to Eq. 2 the information content per hybridization trial of a 3-mer on a 7-mer is 0.4 bits and thus according to Eq. 5 on average at least 40 test oligonucleotides 25 would need to be trial hybridized to target oligonucleotide 20 to derive the de novo sequence information of target oligonucleotide 20.

FIG. 7 gives an example for the general procedure for inverting the sequence showing how both positive hybridization outcomes and negative hybridization outcomes are used to determine sequence. In step 1 a number of test hybridizations as discussed above are carried out. Whether the test oligonucleotide 25 hybridizes or does not is recorded. In step 2 the test oligonucleotide sequences which are recorded to have successfully hybridized are themselves (or as shown in the figure their complement) arrayed into possible target oligonucleotides. This arraying operation is generally carried out in silico although it is possible to carry it out using the techniques of DNA computing known in the literature. As shown in FIG. 7 possible target oligonucleotides which were created with the largest number of overlaps (in this case the most instances of two-base overlaps as opposed to single-base overlaps) are the most likely. In the case of this example there are two possible target oligonucleotides ACGGCCA and CCACGGC which both have been assembled from the set of positively hybridizing test oligonucleotides 25 with two instances of double base overlap and one instance of single base overlap. The two possibilities thus cannot be disambiguated by means of positive hybridizing data alone. In the final step negative hybridizing data, namely data for the set of test oligonucleotides 25 which did not successfully bind to the target oligonucleotide, are used to eliminate possible target oligonucleotide sequences and thus to isolate the correct target oligonucleotide sequence. In this example data that show that test oligonucleotide GTG does not bind target oligonucleotide 20 is used to exclude CCACGGC as a possible target oligonucleotide (otherwise GTG would be expected to hybridize to the CAC portion of CCACGGC) and thus identifies ACGGCCA uniquely as desired target oligonucleotide 20.

FIG. 8 shows a representative series of steps for deriving de novo sequence information from a target oligonucleotide using the set of data (both positive and negative) from a sequence of test oligonucleotide hybridization trials. Those steps include:

selecting an M-Mer test oligonucleotide library as described above;

carrying out sufficient sequential hybridization trials (each including test hybridization of an M-mer test oligonucleotide to an N-mer target oligonucleotide, measuring the positive or negative outcome of the hybridization trial, and, before any subsequence test hybridization, dehybridizing and washing) of members of the M-mer test oligonucleotide library with the N-mer target oligonucleotide such that the hybridization trial information content equals or exceeds the information content of the desired target oligonucleotide;

using positive hybridization outcomes to construct the possible set of target oligonucleotide sequences weighted by the highest degree of overlap; and using negative hybridization outcomes to eliminate members of the possible set of target oligonucleotide sequences.

This set of steps determines the sequence of each individual target oligonucleotide on an inverse DNA chip. In order to get the sequence of the source nucleotide polymer from which the target oligonucleotides were derived (e.g. of an entire genome) a second inverse gene chip from the same genome can be created in which the target oligonucleotides are cut in a different place, preferably far from the original cuts. Target oligonucleotide sequences from both inverse DNA chips may now be assembled in a manner similar to that shown in FIG. 7. Again whole genome sequences created from target oligonucleotide assemblies with maximum overlap are given highest ranking.

EXAMPLE 1

Human Genome

As an example of repetitive single molecule hybridization, we consider the human genome, which includes about 3 billion nucleotide base pairs. Referring to FIG. 6C we choose the 5-Mer test oligonucleotide library with an optimal N-mer size of: ~200 bases. This leads to $15 \times 10^6$ spots (i.e. $K=15 \times 10^6$) equivalent to the number of imaging elements available in current solid state imaging devices or a small array of such imaging devices. Assuming cycle times (hybridization+measurement+wash) of 5 minutes per test oligonucleotide yields a total run time of (1024 test oligonucleotides in the 5-mer test oligonucleotide library)*(5 minutes per cycle)=3.5 days.

EXAMPLE 2

De Novo Synthesis of Nucleic Acids

Regarding another application of the sequencing technology described herein, there has recently emerged considerable interest in the synthesis of long sequences of nucleic acids (See Smith, Hutchison, Pfannkoch, and Venter et al., "Generating a Synthetic Genome by Whole Genome Assembly: phiX174 Bacteriophage from Synthetic Oligonucleotides" *PNAS* 2003). One approach is the chemical synthesis of oligonucleotides followed by their ligation. Unfortunately the error rate for such an approach is equivalent to the chemical synthetic error rate of ~$1:10^2$. One approach is to sequence the ligated product and then perform site directed mutagenesis to correct errors. But as described above this approach is hampered by throughput and cost of current electrophoresis-based sequencing methodologies.

The present invention facilitates accurate synthesis of nucleic acids according to steps comprising:

synthesizing a nucleotide sequence de novo;

a) obtaining sequence information about the synthesized nucleotide sequence by repetitive single molecule hybridization as described above; and c) using site directed mutagenesis to correct at least one error in the synthesized nucleotide sequence.

The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

I claim:

1. A method of obtaining sequence information at N nucleobase positions of a single copy of a target oligonucleotide, the method comprising the steps of:

a) exposing the target oligonucleotide to one or more copies of a test oligonucleotide of M potentially informative nucleobases, wherein (i) if N is less than 50, M is 2, 3, or 4;

(ii) if N is 50-99, M is 3, 4, or 5;

(iii) if N is 100-999, M is 4, 5, or 6;

(iv) if N is 1,000-10,000, M is 5, 6, 7, or 8; and (v) if N is greater than 10,000, M is 7, 8, 9, 10, 11, 12, or 13;

b) measuring the hybridization of the test oligonucleotide to the target oligonucleotide, thereby completing a first hybridization trial;

c) dehybridizing the test oligonucleotide;

d) exposing the target oligonucleotide to one or more copies of at least one additional test oligonucleotide of M potentially informative nucleobases;

e) measuring the hybridization of the additional test oligonucleotide to the target oligonucleotide, thereby completing a further hybridization trial; and f) repeating steps c) to e) until the information content from the hybridization trials exceeds the information content of the target oligonucleotide, wherein the information content from a single hybridization trial is $$I(M, N) = \text{Log}_2\left(\frac{1}{P(M, N)}\right)P(M, N) + \text{Log}_2\left(\frac{1}{1 - P(M, N)}\right)(1 - P(M, N))$$

where P(M,N) is the probability that the M potentially informative nucleobases fully hybridize with a given target oligonucleotide of N nucleobases.

2. The method of claim 1 in which hybridization is measured using a fluorescent tag.

3. The method of claim 1 in which hybridization is measured using a quantum dot or nanoparticle tag.

4. The method of claim 1 in which hybridization is detected mechanically.

5. The method of claim 1 in which hybridization is detected by sensing a change in charge associated with hybridization.

6. The method of claim 5 in which hybridization is detected electronically.

7. The method of claim 1 in which the target oligonucleotide is immobilized on a solid support.

8. The method of claim 1 in which a plurality of target oligonucleotides are immobilized on a solid support.

9. The method of claim 8 in which hybridizations to the plurality of target oligonucleotides are measured substantially in parallel.

10. The method of claim 9 in which the substantially parallel detection is carried out using a solid state imaging device.

11. The method of claim 10 in which the solid state imaging device is used without a lens system in close proximity to the target oligonucleotides.

12. The method of claim 8 in which the target oligonucleotides are immobilized on an inverse nucleotide chip.

13. The method of claim 12 in which the inverse nucleotide chip substantially comprises the genetic material of a genome.

14. A method of synthesizing de novo a nucleic acid sequence, the method comprising the steps of:
    a) synthesizing a nucleic acid sequence de novo;
    b) obtaining information about the nucleic acid sequence by the method of claim 1, thereby to detect an error in the nucleic acid sequence; and
    c) correcting the error in the nucleic acid sequence by site-directed mutagenesis.

15. A method of obtaining sequence information from a single copy of a target oligonucleotide having N nucleobase positions to be queried, the method comprising the steps of:
    a) exposing the target oligonucleotide to one or more copies of a test oligonucleotide of M potentially informative nucleobases;
    b) measuring the hybridization of the test oligonucleotide to the target oligonucleotide, thereby completing a first hybridization trial;
    c) dehybridizing the test oligonucleotide;
    d) exposing the target oligonucleotide to one or more copies of at least one additional test oligonucleotide of M potentially informative nucleobases;
    e) measuring the hybridization of the additional test oligonucleotide to the target oligonucleotide, thereby completing a further hybridization trial;
    f) repeating steps c) to e) until the information content from the hybridization trials exceeds the information content of the target oligonucleotide, wherein the information content from a single hybridization trial is $$I(M, N) = \text{Log}_2\left(\frac{1}{P(M, N)}\right)P(M, N) + \text{Log}_2\left(\frac{1}{1 - P(M, N)}\right)(1 - P(M, N))$$

where P(M,N) is the probability that the M nucleobases fully hybridize with a given target oligonucleotide of N nucleobases;
    g) using positive hybridization outcomes to deduce a set of possible target oligonucleotide sequences; and
    h) using negative hybridization outcomes to eliminate members from the set.

16. The method of claim 15, wherein the set of possible target oligonucleotide sequences is weighted in favor of higher degrees of overlap among sequences detected by the positive hybridization outcomes.

17. A method of obtaining sequence information from a single copy of a target oligonucleotide having N nucleobase positions to be queried, the method comprising the steps of:
    a) exposing the target oligonucleotide to one or more copies of a test oligonucleotide of M potentially informative nucleobases;
    b) measuring the hybridization of the test oligonucleotide to the target oligonucleotide, thereby completing a first hybridization trial;
    c) dehybridizing the test oligonucleotide;
    d) exposing the target oligonucleotide to one or more copies of at least one additional test oligonucleotide of M potentially informative nucleobases;
    e) measuring the hybridization of the additional test oligonucleotide to the target oligonucleotide, thereby completing a further hybridization trial; and
    f) repeating steps c) to e) until the information content from the hybridization trials exceeds the information content of the target oligonucleotide, wherein the information content from a single hybridization trial is computed using the expression $$I(M, N) = \text{Log}_2\left(\frac{1}{P(M, N)}\right)P(M, N) + \text{Log}_2\left(\frac{1}{1 - P(M, N)}\right)(1 - P(M, N))$$

where P(M,N) is the probability that the M nucleobases fully hybridize with a given target oligonucleotide of N nucleobases,
    at least one of the test oligonucleotides comprising a spacer separating at least two of the M potentially informative nucleobases.

18. The method of claim 17, wherein the spacer is a double stranded oligonucleotide region.

19. The method of claim 17, wherein the spacer comprises an abasic furan.

20. The method of claim 17, wherein the spacer comprises a polyethylene glycol.

21. The method of claim 17, wherein the spacer comprises a carbon chain comprising at least three methylene groups.

* * * * *